United States Patent [19]

Garrigue, Roger et al.

[11] Patent Number: 4,999,455

[45] Date of Patent: Mar. 12, 1991

[54] ACRYLIC DERIVATIVE OF UREA

[75] Inventors: Garrigue, Roger; Jack Lalo, both of Toulouse, France

[73] Assignee: Norsolor S.A., Paris la Defense, France

[21] Appl. No.: 345,268

[22] Filed: May 1, 1989

[30] Foreign Application Priority Data

Apr. 29, 1988 [FR] France ................................ 88 05745

[51] Int. Cl.$^5$ .......................................... C07C 275/20
[52] U.S. Cl. ........................................ 564/59; 528/246
[58] Field of Search ........................... 564/59; 528/246

[56] References Cited

FOREIGN PATENT DOCUMENTS 2580635  10/1986  France .

OTHER PUBLICATIONS

Formaldehyde by J. F. Walker, American Chemical Society Monograph Series, Reinhold Publishing Corporation, p. 374, 3rd edition, London.

Primary Examiner—John Kight, III
Assistant Examiner—Kathryne Shelborne
Attorney, Agent, or Firm—Millen, White & Zelano

[57] ABSTRACT

New acrylic derivative of urea: monomethylolacrylamidomethyleneurea.

Preparation process, according to which acrylamidomethyleneurea is reacted with formaldehyde.

Application to the manufacture of additives suitable for use in aminoplastic resins.

6 Claims, 3 Drawing Sheets

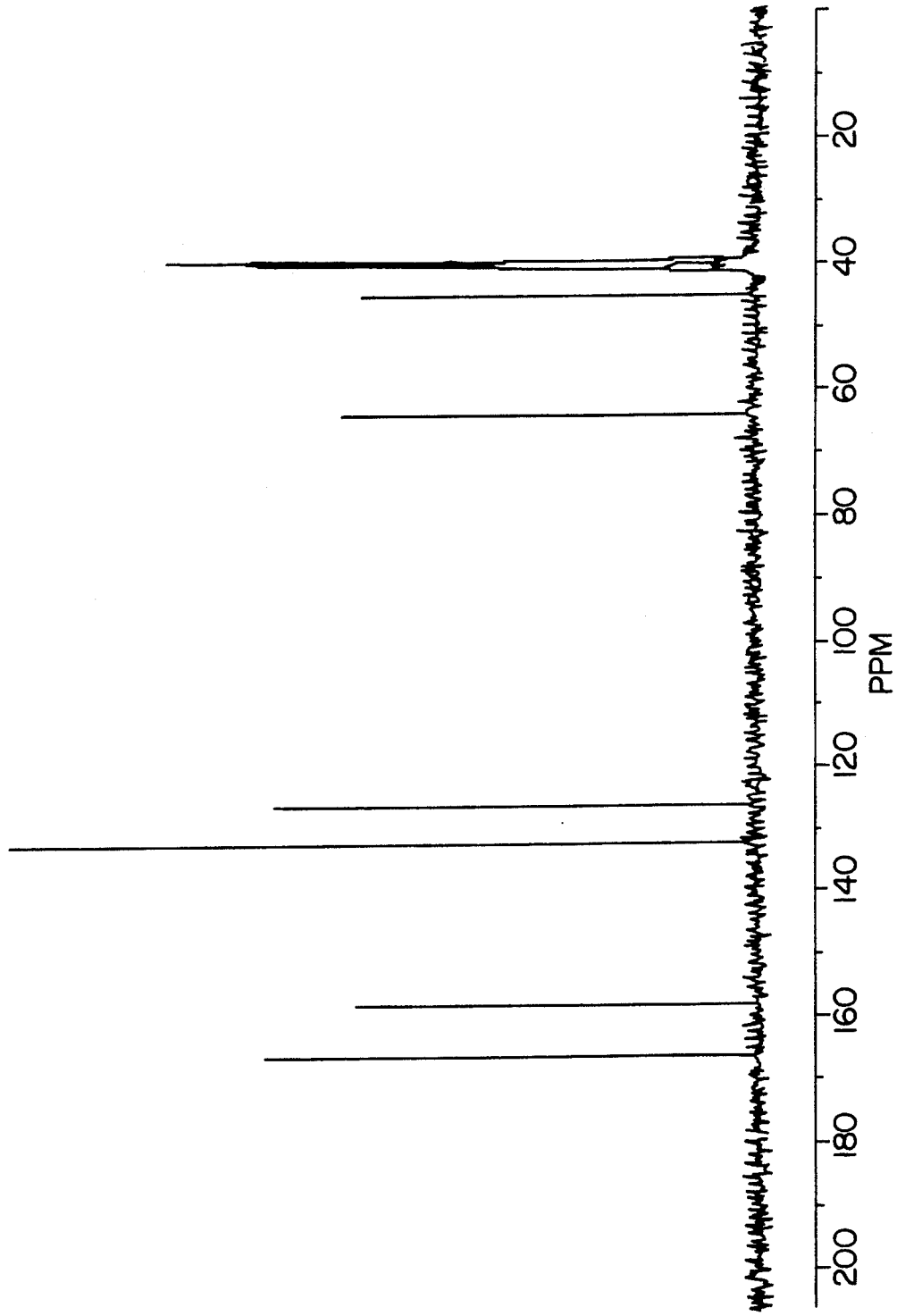

ACRYLIC DERIVATIVE OF UREA

CROSS-REFERENCE TO RELATED APPLICATIONS

This application is related to applicants' concurrently filed United States applications entitled: "New Process for Manufacturing Urea/Formaldehyde Resins," U.S. Ser. No. 07/345279, and "New Additives for Use in Aminoplast Resins," U.S. Ser. No. 07/345267, priority based on respective French Applications 88/05,746 and 88/05,744, both filed Apr. 29, 1988.

BACKGROUND OF THE INVENTION

The present invention relates to a new acrylic derivative of urea.

Acrylic derivatives of urea are already known. The acrylic compounds used as starting substances are most often acrylamide and acrylonitrile. Thus, the polycondensation of urea, formaldehyde and acrylamide in a weakly alkaline medium with a view to preparing methylolated products, followed by the addition of styrene or methyl acrylate, has been proposed (in particular, Kostyukov et al—USSR 277,550, 3 June 1970). The preparation of acrylic derivatives of urea from methacrylamide, formaldehyde and urea has also been proposed (French Application 85/06,106). A new process for manufacturing acrylamidomethyleneurea has also been described (in French Application 85/06,103), which process consists in reacting, in a first stage, acrylamide with formaldehyde in a basic medium with a view to obtaining monomethylolacrylamide, and then, in a second stage, in reacting the latter compound with urea in an acid medium.

The present invention relates to a new acrylic derivative of urea, monomethylolacrylamidomethyleneurea.

This product has the following formula:

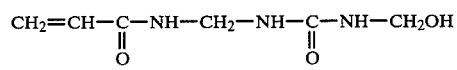

This product takes the form of a white solid which changes its physical state between 190 and 200° C.

The new acrylic derivative of urea is prepared according to the following procedure. According to this procedure, acrylamidomethyleneurea, obtained according to the preparation process described in French Application 85/06,103, is employed. This process comprises a first step of reacting acrylamide with formaldehyde at a basic pH and then in a second step reacting the resultant product from the first step with urea at a pH of at most 4.5, the quantity of urea being preferably higher than 4 molar equivalents to one molar equivalent of the reaction product obtained in the first step.

To this resultant urea derivative, water and aqueous solution of formaldehyde are added. The reaction is carried out in the presence of an inhibitor such as hydroquinone methyl ether and triethylamine, heating for approximately one hour to 60° C. A white precipitate is then formed after cooling, and is separated by filtration. The product is then purified by washing with ethyl acetate and then with acetone: it is then recrystallized in an ethyl acetate/ethanol mixture.

The new acrylic derivative which is the subject of the invention is prepared using equimolecular quantities of acrylamidomethyleneurea and formaldehyde. It is especially useful as an additive in aminoplastic and phenoplastic resins, in particular those used as wood glues. In aminoplastics in particular, it is employed in the form of a solution in a urea/formaldehyde precondensate. In this case, the monomethylolacrylamidomethyleneurea dissolved in a urea/formaldehyde precondensate is prepared according to the procedures described in the above-cross-referenced application entitled "New Additives Suitable for use in Aminoplastic Resins." These procedures consist in preparing monomethylolacrylamidomethyleneurea either from acrylamide in a urea/formaldehyde precondensate, or from acrylamidomethyleneurea in a urea/formaldehyde precondensate.

BRIEF DESCRIPTION OF DRAWINGS

The attached FIGS. 1, 2 and 3 are graphs directed to infrared spectrum, proton NMR and carbon 13 NMR, respectively.

EXAMPLES

Figure 1:
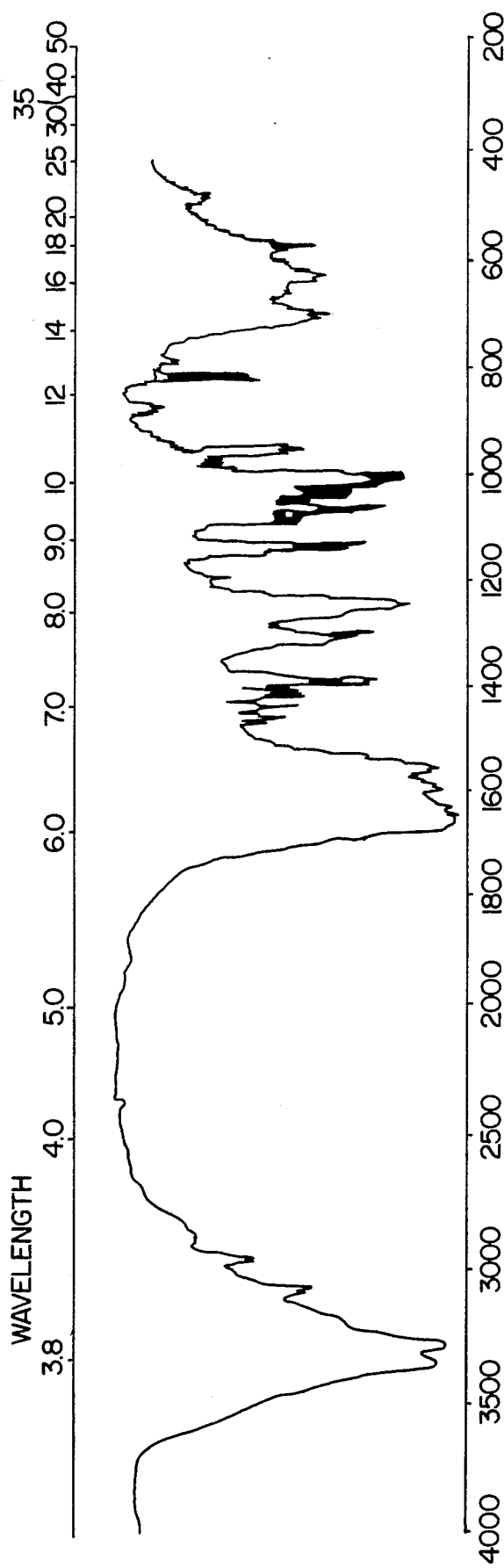

The following examples illustrate the present invention:

EXAMPLE 1

The starting material acrylamidemethyleneurea is prepared by introducing into an agitated reactor provided with a reflux condensor, the following charge: 20 parts of acrylamide, 22.8 parts of a 37% aqueous formaldehyde solution, 0.2 parts of triethylamine, and 0.01 parts of hydroquinone methyl ether. The reaction is maintained at 50° C. for one hour. In a second step, after the resultant reaction product from the first step is cooled to 10° C., there are added 67.6 parts of urea and 15 parts of concentrated hydrochloric acid. The pH of the resultant reaction milieu is then 1. The reaction milieu is agitated for 15 hours at ambient temperature, thereby forming a precipitate as the reaction proceeds. The resultant product is filtered and recrystallized in water, thereby obtaining 27.5 parts of acrylamidomethyleneurea.

Preparation of monomethylolacrylamidomethyleneurea 11.34 g of a 37% strength aqueous solution of formaldehyde, 40 g of water, 20 g of acrylamidomethyleneurea, 50 mg of hydroquinone methyl ether and 0.2 g of triethylamine are introduced into a 250-ml reactor. The reaction mixture is heated for 1 hour to 60° C.

A homogeneous and clear reaction mixture is obtained, and this is cooled to room temperature. A white precipitate is then formed which is separated by filtration, then washed with ethyl acetate and then with acetone. It is then recrystallized in an ethyl acetate/ethanol (10:90) mixture.

| quantity product obtained | m = 15.7 g |
|---|---|
| yield | = 65% |

The product has the appearance of a white powder; when heated on a Kofler stage, a change in its physical state occurs at between 190 and 200° Celsius. Elemental analysis carried out on the product gave the following results:

| nitrogen | 24.15% | (theory 24.27%) |
|---|---|---|
| carbon | 41.9% | (theory 41.6%) |

| | -continued | |
|---|---|---|
| hydrogen | 6.2% | (theory 6.36%) |

EXAMPLE 2

Monomethylolacrylamidomethyleneurea dissolved in a urea/formaldehyde precondensate is prepared according to the procedure described in the cross-referenced application "New Additives Suitable for Use in Aminoplastic Resins."

60 g of pure acrylamidomethyleneurea, 120 mg of hydroquinone methyl ether and 350 g of a urea/formaldehyde precondensate, prepared from a 49% strength solution of formaldehyde and a 20% strength solution of urea, are introduced into a reactor. The pH of the reaction medium is maintained at 7.5, and the reaction is carried out at 70° C. until the acrylamidomethyleneurea is solubilized.

The methylolated derivative thereby obtained in a urea/formaldehyde precondensate is used as an additive in a urea/formaldehyde resin.

DETAILED DESCRIPTION OF FIGURES

Figure 2:
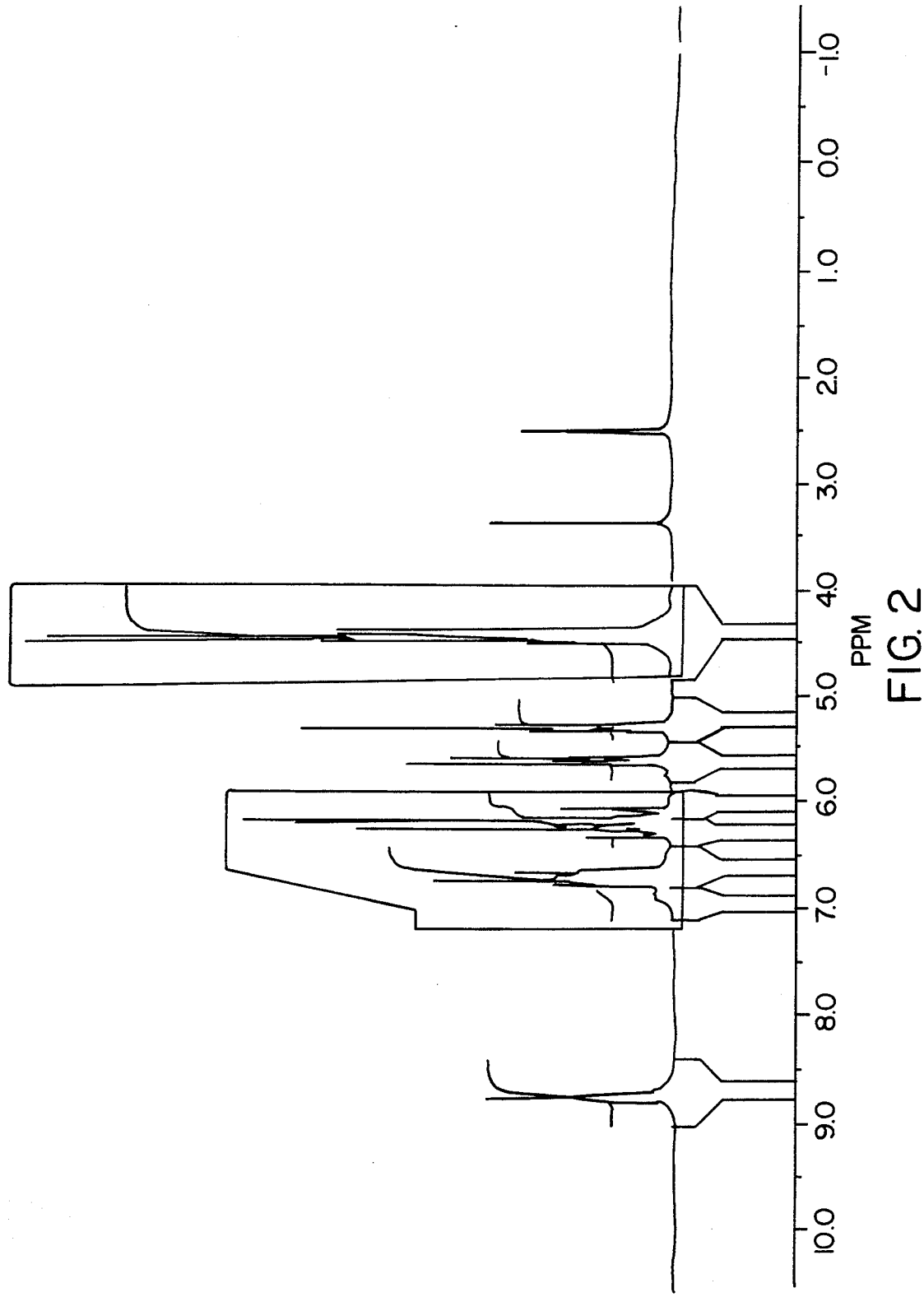

The infrared spectrum (FIG. 1) and proton NMR (FIG. 2) and carbon-13 NMR (FIG. 3) spectra in deuterated DMSO enable the structure of the monomethylolacrylamidomethyleneurea to be confirmed.

Without further elaboration, it is believed that one skilled in the art can, using the preceding description, utilize the present invention to its fullest extent. The foregoing specific embodiments are, therefore, to be construed as merely illustrative, and not limitative of the disclosure herein in any way whatsoever.

In the foregoing, all temperatures are set forth uncorrected in degrees Celsius and, unless otherwise indicated, all parts and percentages are by weight.

The entire texts of all applications, patents and publications cited above, and of corresponding Application 88/05,745 filed Apr. 29, 1988 in France, are herein incorporated by reference.

We claim:

1. A monomethylolacrylamidomethyleneurea of the formula:

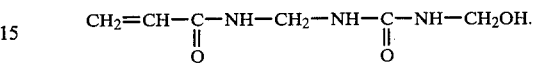

2. A process for preparing monomethylolacrylamidomethyleneurea according to claim 1, characterized in that acrylamidomethyleneurea is reacted with formaldehyde in the presence of an inhibitor.

3. A process for preparing monomethylolacrylamidomethyleneurea according to claim 2, characterized in that equimolecular quantities of acrylamidomethyleneurea and formaldehyde are used.

4. A process according to claim 3 prepared in the presence of water and wherein the inhibitor is at least one of hydroquinone methyl ether and triethylamine.

5. A process according to claim 4 conducted in the presence of both hydroquinone methyl ether and trimethylamine.

6. A process according to claim 5, wherein the reaction is conducted for approximately one hour at 60° C.

* * * * *